US010196659B2

(12) United States Patent
Alphand et al.

(10) Patent No.: US 10,196,659 B2
(45) Date of Patent: Feb. 5, 2019

(54) **METHOD FOR PRODUCING LACTONES FROM A STRAIN OF *AUREOBASIDIUM PULLULANS***

(71) Applicant: CHARABOT, Grasse (FR)

(72) Inventors: Véronique Alphand, Marseilles (FR); Alain Archelas, Marseilles (FR); Eva Boukhris-Uzan, Marseilles (FR); Elise Courvoisier-Dezord, Les Pennes Mirabeau (FR); Sophie Lavoine-Hanneguelle, Mouans Sartoux (FR)

(73) Assignee: CHARABOT, Grasse (FR)

( * ) Notice: Subject to any disclaimer, the term of this patent is extended or adjusted under 35 U.S.C. 154(b) by 0 days.

(21) Appl. No.: 15/121,515

(22) PCT Filed: Feb. 26, 2015

(86) PCT No.: PCT/FR2015/000042
§ 371 (c)(1),
(2) Date: Aug. 25, 2016

(87) PCT Pub. No.: WO2015/128552
PCT Pub. Date: Sep. 3, 2015

(65) Prior Publication Data
US 2016/0362712 A1 Dec. 15, 2016

(30) Foreign Application Priority Data

Feb. 27, 2014 (FR) ...................................... 14 00499

(51) Int. Cl.
C12P 17/06 (2006.01)
C12P 7/64 (2006.01)
(52) U.S. Cl.
CPC ............. *C12P 17/06* (2013.01); *C12P 7/6409* (2013.01)
(58) Field of Classification Search
None
See application file for complete search history.

(56) References Cited

U.S. PATENT DOCUMENTS 5,399,720 A * 3/1995 Karpf ................... C07D 305/12
549/292
6,060,507 A * 5/2000 Hill ........................ A01N 43/16
514/460

FOREIGN PATENT DOCUMENTS

| JP | 63-57583 A | 3/1988 |
| JP | 63-215676 A | 9/1988 |
| JP | 63-222164 A | 9/1988 |
| JP | 2-59564 A | 2/1990 |
| JP | 9-31071 A | 2/1997 |
| JP | 3779751 B2 | 5/2006 |

OTHER PUBLICATIONS

Singh et al. (Appl. Microbiol. Biotechnol., 2007, vol. 75, p. 713-722).*
Girskov et al. (J. Bacteriol., Nov. 1996, vol. 178, No. 22, pp. 6618-6622).*
Levene et al. (J. Biol. Chem., 1926, vol. 68, pp. 737-749).*
Parker et al. (J. Argic. Food, Chem., 1997, vol. 45, pp. 2774-2776).*
Kurosawa et al., "Extracellular Accumulation of the Polyol Lipids, 3,5-Dihydroxydecanoyl and 5-Hydroxy-2-decenoyl Esters of Arabitol and Mannitol, by *Aureobasidium* sp.", Biosci. Biotech. Biochem., vol. 58, No. 11, 1994, pp. 2057-2060; cited in the ISR, Specification and priority French Search Report.
Abelovska et al., "Comparison of element levels in minimal and complex yeast media", Can. J. Microbiol, vol. 53, 2007, pp. 533-535; cited in the ISR and priority French Search Report.
Grant et al., "Minor Element Composition of Yeast Extract", Journal of Bacteriology, American Society for Microbiology, vol. 84, 1962, pp. 869-870; cited in the priority French Search Report.
Price et al., "Structural characterization of novel extracellular liamocins (mannitol oils) produced by Aureobasidium pullulans strain NRRL 50380", Carbohydrate Research, vol. 370, 2013, pp. 24-32; cited in the Specification.
French Search Report dated Nov. 4, 2014 issued in corresponding priority application No. FR1400499; w/ English machine translation (12 pages).
International Search Report and Written Opinion dated Jul. 16, 2015 issued in corresponding application No. PCT/FR2015/000042; w/ English partial translation and partial machine translation (17 pages).
Pennapa Manitchotpisit et al., "Multilocus phylogenetic analyses, pullulan production and xylanase activity of tropical isolates of Aureobasidium pullulans", Mycological Research (2009) 113:1107-1120 (in English).
Pennapa Manitchotpisit et al., "Heavy oils produced by Aureobasidium pullulans", Biotechnol. Lett. (2011) 33:1151-1157 (in English).
Pennapa Manitchotpisit et al., "Poly(beta-L-malic acid) production by diverse phylogenetic clades of Aureobasidium pullulans", J. Ind. Microbiol. Biotechnol. (2012) 39:125-132 (in English).

* cited by examiner

*Primary Examiner* — Hope Robinson
(74) *Attorney, Agent, or Firm* — Westerman, Hattori, Daniels & Adrian, LLP

(57) ABSTRACT

The invention relates to a method for producing lactones from a strain of *Aureobasidium pullulans* that are produced from a pre-culture of the *Aureobasidium pullulans* strain CBS 771.97, obtained from CBS-KNAW Fungal Biodiversity Center, Uppsalalaan 8, 3584 CT Utrecht, Netherlands, or related strains; from an inoculum obtained from the pre-culture; a culture is produced by fermentation at a temperature between 20° C. and 40° C. over a period of at least 3 days so as to produce metabolites, in a sterilized aqueous production medium containing: a carbon source; a nitrogen source; a mineral salt solution; and a calcium source, at a concentration between 2 and 100 mM; and following the fermentation period, converting the metabolites produced into a lactone mixture comprising (R)-5,6-dihydro-6-pentyl-2H-pyran-2-one (or (R)-(−)-*massoia* lactone) and/or (4R,6R)-4-hydroxy-6-pentyl-tetrahydro-2H-pyran-2-one.

22 Claims, 4 Drawing Sheets

METHOD FOR PRODUCING LACTONES FROM A STRAIN OF *AUREOBASIDIUM PULLULANS*

The invention relates to a method for producing lactones from a strain of *Aureobasidium pullulans*, and more particularly (R)-5,6-dihydro-6-pentyl-2H-pyran-2-one, commonly known as (R)-(−)-*massoia* lactone.

As a general rule, a lactone is an oxygenated heterocycle, obtained from the cyclization (or lactonization) of hydroxyacids. The main lactones comprise rings between 4 and 12 carbon atoms. The diversity thereof lies in the chirality of these molecules, the nature of the lateral groups, and the presence or not of unsaturation at the lateral chain or the ring (Dufossé et al., Importance des lactones dans les arômes alimentaires: structure, distribution, propriétés sensorielles et biosynthèse, 1994).

Lactones are aromatic compounds contained in a wide variety of food products and beverages.

More particular interest is focused on *massoia* lactone. It is found in the form of an enantiomer mixture in variable proportions. To avoid any doubt, unless specified otherwise, both forms are intended to be covered by the term *massoia* lactone as used in the present application.

More particular interest is focused on (R)-(−)-*massoia* lactone, also known as (R)-5,6-dihydro-6-pentyl-2H-pyran-2-one or cocolactone, having the following chemical structure:

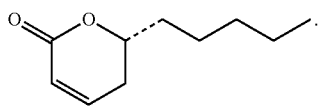

*Massoia* lactone is an alkyl lactone obtained from the bark oil of the *Cryptocaria massoia* tree (Abe et al., Studies on the Essential Oil of Masooi, 1937; or Rali et al., Comparative chemical analysis of the essential oil constituents in the bark, heartwood and fruits of *Cryptocarya* massoy (Oken) Kosterm. (Lauraceae) from Papua New Guinea, 2007) which is particularly found in Indonesia.

For example, it is found to be commercially available from Charabot as *Cryptocaria massoia* tree bark extract.

This compound may also be found as a constituent of sugar cane molasses (Hashizume et al., Constituents of Cane Molasses, 1968), dried tobacco and the essential oil of *Osmanthus fragrans*.

*Massoia* lactone is primarily known for the odor thereof described as having a sweet, creamy, milky and waxy scent of coconut, and the taste thereof described as a creamy and slightly fruity coconut flavor. To this effect, it is widely used due to the intrinsic features thereof in a wide range of fields such as for example food products.

It is also known for the use thereof as an antifungal (patent document U.S. Pat. No. 6,060,507) or for the role thereof in attracting insects and thus facilitating spore dispersal (Nago et al., An ecological role of volatiles produced by *Lasiodiplodia theobromae*, 1994).

*Massoia* lactone is commonly manufactured by extraction from *Cryptocaria massoia* or by synthesis.

However, the current plant-based production method frequently gives rise to the felling of a large number of trees, and is not suitable for an extensive supply. Furthermore, such a method is subject to environmental constraints in that the tree is frequently killed during the debarking process and gives rise to very high production costs based on natural products.

*Massoia* lactone may thus be alternatively synthesized chemically both in the racemate form (e.g. Garnero et al., Flavouring substances: design of 6-alkyl-(and 6,6-dialkyl-) 5,6-dihydro-2-pyrones, 1986; or JP 63-57583, JP 63-215676, JP 63-222164) or enantiomer form (e.g. Yu et al., Enantioselective total synthesis of 6R-(−)*massoia* lactone, 1993; Takano et al., An enantiospecific route to (6R)-(−)-*massoia* lactone and (4R,6R)-(+)-4-hydroxy-6-pentylvalerolactone, 1992; Bennett et al., Total syntheses of natural (+)-(4R,6R)-4-hydroxy-6-pentylvalerolactone and of (−)-(6R)-*massoia* lactone, 1991; Pirkle et al., Enantiomerically pure lactones, 1980; patent document JP02059564; Hoeyer et al., A convenient synthesis of homochiral delta alkylated alpha,beta unsaturated delta-lactone, 1991; Fehr et al., Novel approach to the synthesis of 6-substituted 5,6-dihydro-2 (2H)-pyranones, 1981; and Pan et al., An efficient and stereoselective synthesis of (−)-*massoia* lactone, 1996; or JPH0259564).

However, it is important to note that the odor of *massoia* lactone differs between the (R)-(−)-*massoia* lactone and (S)-(+)-*massoia* lactone form. Indeed, the (S)-(+)-*massoia* lactone form has a buttery odor whereas the (R)-(−)-*massoia* lactone form has a characteristic coconut fragrance (Nohira et al., Optical Resolution of Fragrant Lactones, 2000). Consequently, in order to meet requirements, it is essential use a method suitable for manufacturing the (R)-(−)-*massoia* lactone form with a high optical purity.

However, it is relatively costly to develop and use such synthesis methods due in particular to the constraints associated with the choice of starting materials and with each of the steps to obtain the (R)-(−)-*massoia* lactone form with a high optical purity.

Furthermore, obtaining by chemical synthesis meets consumer demands less and less.

An alternative solution is necessary: the production of lactones in general, and more particularly of (R)-(−)-*massoia* lactone, by a biotechnological process. It is possible for example to use microbial cells and enzymes to biotransform or bioconvert fatty acids into lactones. Various studies and patent documents have been published on this subject.

The patent document JP3779751 is known, which discloses a simple method for manufacturing (R)-(−)-*massoia* lactone from the culture of a microorganism, and more particularly of the marine microorganism *Exophiala pisciphila* N1-10102 (registered with Fermentation Research Institute (Agency of Industrial Science and Technology) in Japan, under the number P-14232). Such a method is suitable for generating (R)-(−)-*massoia* lactone in the reaction medium and retrieving (R)-(−)-*massoia* lactone by means of a separation step. The culture medium used comprises a source of nitrogen such as L-asparagine, a source of carbon such as glucose and minerals such as sodium chloride, potassium chloride, potassium dihydrogen phosphate but does not comprise calcium, and after 5-10 days of culture at 22-27° C. at pH 6-7, the medium is acidified by an acid such as sulfuric acid in the presence of a solvent such as methanol and heated to obtain (R)-(−)-*massoia* lactone in the reaction medium.

Also, the yield obtained disclosed in this document is merely 1.4 mg/100 mL i.e. 14 mg/L.

The Price et al. publication (Structural characterization of novel extracellular liamocins (mannitol oils) produced by *Aureobasidium pullulans* strain NRRL 50380, 2013) is also known, which discloses a method for obtaining *massoia* lactone from liamocins extracted from the culture of the *Aureobasidium pullulans* strain NRRL 50380 in a medium containing 5% (weight/volume) sucrose. The liamocins are extracted using a methyl ethyl ketone and the maximum yield is obtained on day 6 with a yield between 0.5 and 6 g of mannitol oil (liamocins)/L. *Massoia* lactone is then obtained after methanolysis with anhydrous methanol in the presence of hydrochloric acid, centrifugation so as to eliminate a heavy white precipitate and retrieve the methanol-soluble fraction comprising *massoia* lactone.

Furthermore, the Kurosawa et al. publication (Extracellular accumulation of the polyol lipids, 3,5-dihydroxydecanoyl and 5-hydroxy-2-decenoyl esters of arabitol and mannitol, by *Aureobasidium* sp. 1994) is known. This publication discloses that numerous *Aureobasidium pullulans* strains produce large quantities of poly(β-L-malic acid) in a medium containing calcium carbonate $CaCO_3$. This publication reveals that, in the absence of $CaCO_3$ in the culture medium, these strains produce extracellular lipids such as heavy oils instead of poly(malic acid). This publication describes more particularly obtaining (+)-3-hydroxydecan-5-olide and R-(−)-*massoia* lactone from the culture of the *Aureobasidium pullulans* strain A-21M for 7 days at 25° C. in a medium containing 12% glucose, 0.15% $NaNO_3$, 0.10% $KNO_3$, 0.005% $KH_2PO_4$, 0.02% $MgSO_4$ $7H_2O$, 2 ppm $ZnSO_4$ $7H_2O$ and 0.02% yeast extract in deionized water, this medium thus not comprising $CaCO_3$. 35 g of heavy oils comprising lipids are extracted with methyl ethyl ketone. Approximately 10 g of lipids are saponified by adding sodium hydroxide NaOH followed by a hydrolysis by adding sulfuric acid $H_2SO_4$ to retrieve approximately 4 g of fatty acids. The compounds (+)-3-hydroxydecan-5-olide and R-(−)-*massoia* lactone are finally retrieved by extraction with ether.

However, it can be inferred that the R-(−)-*massoia* lactone yield obtained in this way is low in relation to the 35 g of heavy oils comprising lipids isolated according to this method. On the basis of the results mentioned in this document, the R-(−)-*massoia* lactone yield is 1.3 g/L.

In view of the above, one problem addressed by the invention is that of developing an alternative method for producing lactones, more particularly (R)-(−)-*massoia* lactone which is suitable for use as such, from a strain of *Aureobasidium pullulans*, which is easy to implement, inexpensive and which has a satisfactory reproducibility, from sustainable and natural resources, and enhanced productivity (enhanced quantity of lactone of interest and production rate).

The invention thus relates to a method for producing lactones from a strain of *Aureobasidium pullulans*, characterized in that it comprises the following steps whereby:

a pre-culture of the *Aureobasidium pullulans* strain CBS 771.97 (obtained from CBS-KNAW Fungal Biodiversity Centre, Uppsalalaan 8, 3584 CT Utrecht, Netherlands) or the related strains thereof is produced;

from an inoculum obtained from the pre-culture, a culture is produced by fermentation at a temperature between 20° C. and 40° C. over a period of at least 3 days so as to produce metabolites, in a sterilized aqueous production medium containing:
a carbon source;
a nitrogen source;
a mineral salt solution; and
a calcium source, at a concentration between 2 and 100 mM; and following the fermentation period, the metabolites produced are converted into a lactone mixture comprising (R)-5,6-dihydro-6-pentyl-2H-pyran-2-one and/or (4R, 6R)-4-hydroxy-6-pentyl-tetrahydro-2H-pyran-2-one.

The invention and the advantages resulting therefrom will be understood more clearly on reading the description and the non-limiting embodiments hereinafter, with reference to the appended figures wherein.

Figure 6:
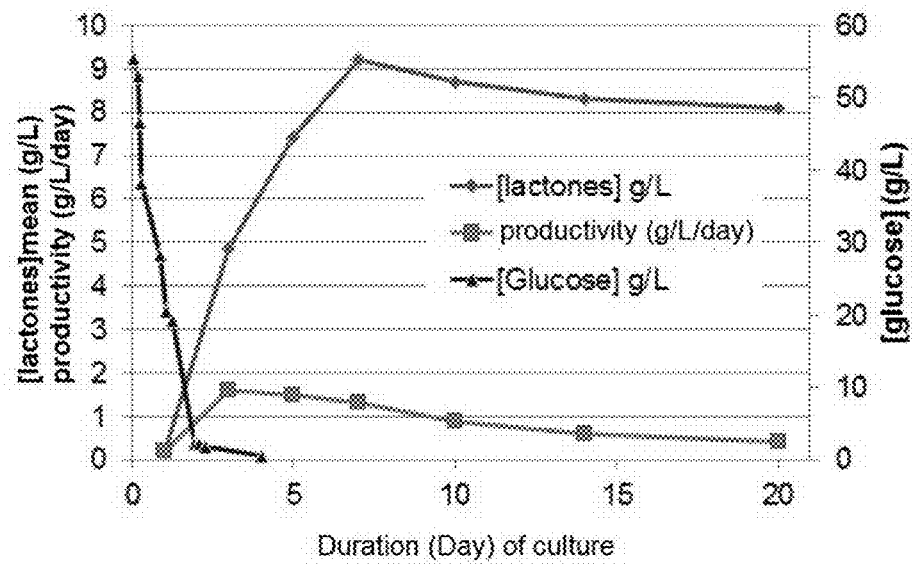
Figure 7:
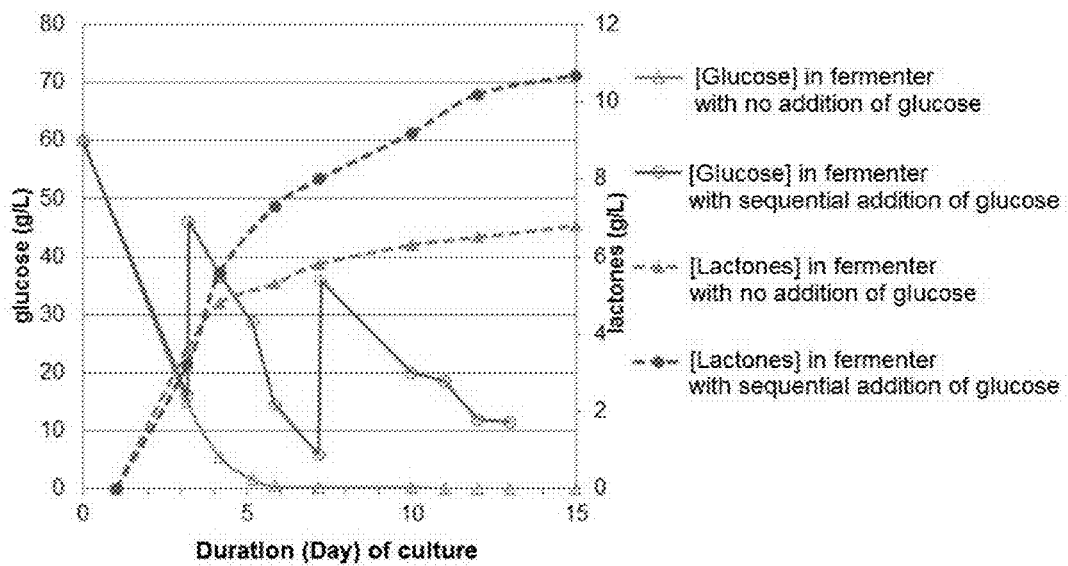

FIG. 6 is a graph representing the monitoring of lactone production, productivity and glucose consumption according to any example of the method according to the invention for the *Aureobasidium pullulans* strain CBS 771.97; and FIG. 7 is a graph representing the effect of the sequential addition of glucose into the medium during the culture step on lactone production and productivity according to an example of the method according to the invention for the *Aureobasidium pullulans* strain CBS 771.97.

In this description, unless specified otherwise, it is understood that, when an interval is given, it includes the upper and lower limits of said interval.

The method according to the invention is used for lactone production from a strain of *Aureobasidium pullulans*.

The method used according to the invention was developed so as to enable reproducibility of the cultures and analyses of the metabolites produced.

*Aureobasidium pullulans* is an ascomycetes type polymorphic ubiquitous fungus. This fungus, frequently in the form of a black yeast, has a complex reproduction cycle, comprising varied unicellular forms (yeast, blastospore, chlamydospore type cells) and a filamentous mycelial form during which the individual hyphae produce unicellular cells by budding. These different physiological states coexist in varied proportion according to the culture conditions (carbon and nitrogen sources, pH, oxygen and mineral salt concentration, etc.).

The Applicant sought to control the reproduction cycle of *Aureobasidium pullulans*, and more particularly of the *Aureobasidium pullulans* strain CBS 771.97 (obtained from CBS-KNAW Fungal Biodiversity Centre, Uppsalalaan 8, 3584 CT Utrecht, Netherlands) or the related strains thereof.

The term related strain to the *Aureobasidium pullulans* strain CBS 771.97 according to the invention denotes an *Aureobasidium pullulans* strain belonging to the same clade as the CBS 771.97 strain. In phylogenetic terms, a clade is defined by a set of organisms forming a monophyletic group, i.e. having a common ancestor and including all the descendants thereof. As such, species of the same clade will always be closer to each other than another species outside the clade. Members of the same clade have at least one characteristic inherent to the entire group, which was inherited from a common ancestor. The distribution of the strains of *Aureobasidium* in different clades is based on the percentage of similarity of the beta-tubulin gene (BT2) sequence thereof, along with that defined by Manitchotpisit et al. (Multilocus phylogenetic analyses, pullulan production and xylanase activity of tropical isolates of *Aureobasidium pullulans*, 2009; Heavy oils produced by *Aureobasidium pullulans*, 2011; and Poly(β-L-malic acid) production by diverse phylogenetic clades of *Aureobasidium pullulans*, 2012). As such, *Aureobasidium* strains belonging to the same clade have greater mutual similarities in respect of the beta-tubulin gene sequences than those belonging to another clade.

Within the scope of the invention, we apply the criteria defined by Manitchotpisit et al. to determine the related strains and on the basis of this classification, the CBS 771.97 strain thus belongs to clade No. 7.

Figure 1:
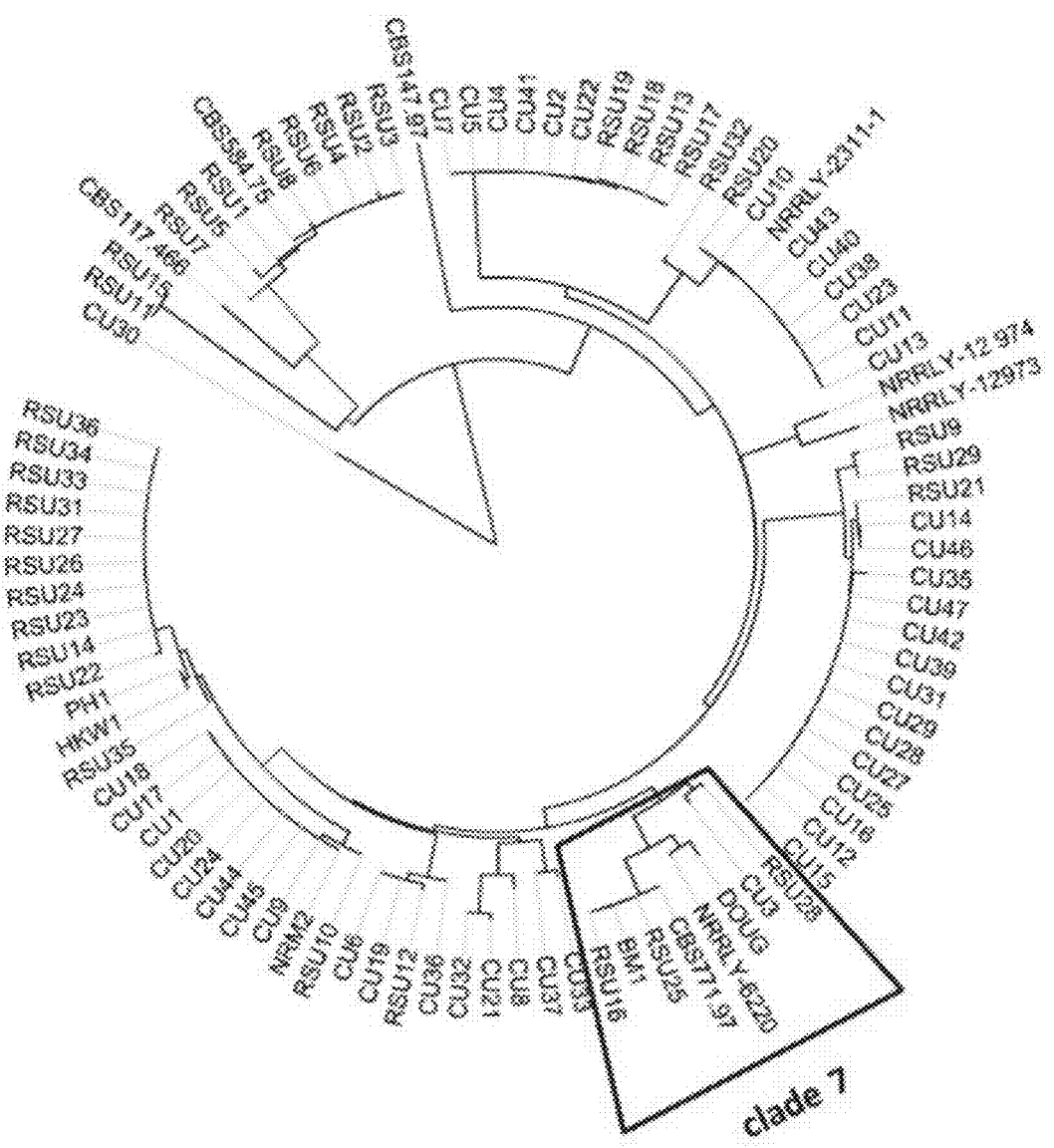
FIG. 1 represents a phylogenetic tree (constructed with ClustalW™ and iTol™) of the *Aureobasidium* genus based on the partial sequences of the beta-tubulin gene registered in the GenBank® database or sequenced by the Applicant.

By way of non-limiting example of a strain related to the CBS 771.97 strain belonging to clade No. 7, mention may be made of the *Aureobasidium* genus strains RSU28, CU3, DOUG, NRRLY-6220, RSU25, BM1, RSU16 as represented in FIG. 1.

According to the invention, it is particularly advantageous to obtain the yeast form which makes it possible to work in a more homogenous medium and is thus more favorable for satisfactory reproducibility. The filamentous form is much more difficult to handle which has a significant impact on fermentation reproducibility. Furthermore, the filamentous form only produces little or no lactone precursor metabolites.

A pre-culture step was introduced so as to be able to start from a batch (inoculum) of the same quantity of cells in the same physiological state for each culture. Indeed, it is practically impossible to obtain synchronous growths in a single step. Although pre-culture steps are relatively conventional practices in microbiology, the respective durations of each step and the choice of pre-culture medium and the temperature were adapted to the *Aureobasidium pullulans* strain CBS 771.97 or the related strains thereof, used according to the invention to control the form wherein it is developed, preferentially the yeast form in relation to the filamentous form.

As such, in a first step of the method according to the invention, a pre-culture of the *Aureobasidium pullulans* strain CBS 771.97 or the related strains thereof is produced, using for example a cryotube of this strain stored at −80° C.

The pre-culture step is preferentially carried out in a solid and/or liquid medium chosen from a medium based on malt extract, for example Malt Extract Fluka™ no 70167 (Sigma-Aldrich) or Malt Extract™ (MP Biomedicals), and advantageously peptones, for example Bacto™ peptone (Difco), or a YNB ("Yeast Nitrogen Base") medium, for example Difco™ Yeast Nitrogen Base.

Preferentially, the pre-culture step comprises at least one first pre-culture step in a solid medium so as to control the state of development of the microorganism and ensure reproducibility, and at least one second pre-culture step in a liquid medium to enable the microorganism to adapt to a liquid medium and control the form of the microorganism (particularly yeast) and cell production for culture.

By way of example, the pre-culture step advantageously comprises the following steps whereby:

using a cryotube of the *Aureobasidium pullulans* strain CBS 771.97 or the related strains thereof, a malt extract peptone agar tube is inoculated, incubated at 25° C. until colonies appear;

using this tube, a Petri dish containing a malt extract peptone agar is inoculated in streaks, incubated at 25° C. for 24 hours; and after growth on the dish, a clone is inoculated in a liquid malt extract tube, incubated at 25° C. under stirring at 200 rpm for approximately 18 hours.

This advantageous pre-culture step is subsequently used for inoculating a flask of bioreactor/fermenter for the fermentation culture step of the *Aureobasidium pullulans* strain CBS 771.97 or the related strains thereof in a liquid production medium and under conditions defined according to the invention.

Obviously, insofar as the culture step is carried out in a bioreactor/fermenter of 1 liter to more than 1000 liters suitable for optimizing the control of the culture conditions and increasing the quantities of metabolites produced, the pre-culture steps may be multiplied so as to obtain the quantities/volumes of inoculum sought.

Using an inoculum obtained from the pre-culture, a culture is then produced by fermentation at a temperature between 20° C. and 40° C. for a period of at least 3 days so as to produce metabolites, more particularly sucrolipids, in a sterilized aqueous production medium containing a carbon source, a nitrogen source, a mineral salt solution, and a calcium source, and optionally a vitamin source.

Preferentially, the pre-culture volume of the *Aureobasidium pullulans* strain CBS 771.97 or the related strains thereof inoculated in the liquid production medium relates to an initial Optical Density (OD) of the culture medium, comprising the production medium and the inoculum, between 0.5 and 2, more preferentially an initial OD of 0.5.

The volume of the inoculum is preferentially between 3 and 10% of the volume of the culture medium.

The fermentation culture step is preferentially carried out at a temperature of 25° C. to 35° C., more preferentially between 28° C. and 30° C., for example at 30° C.

Furthermore, the fermentation culture step is preferentially carried out under stirring for a period of 3 to 20 days, more preferentially of 5 to 18 days, even more preferentially of 7 to 15 days, for example 7 days, 10 days, 12 days, 14 days or 15 days.

By way of illustrative example, when the fermentation is carried out in a 300 mL baffled flask filled to 10% with production medium, the stirring is constant, in the region of 140 rpm. In a fermenter, the stirring may be for example in the region of 500 rpm.

Advantageously, the aeration also has an influence, and may be for example in the region of 0.5 vvm during culture in a bioreactor/fermenter.

However, the stirring speed and aeration chosen are dependent on the geometry of each fermenter. As such, in fermenter/bioreactors, those skilled in the art will take care to adjust the aeration and stirring parameters so as to obtain oxygenation at least equivalent to that of a flask.

The sterilized aqueous production medium used in the culture step by fermentation of the *Aureobasidium pullulans* strain CBS 771.97 or the related strains thereof according to the invention contains a carbon source, a nitrogen source, a mineral salt solution, a calcium source, and optionally a vitamin source.

The flask or the bioreactor/fermenter is filled with the sterilized aqueous production medium, followed by the inoculum to form the culture medium.

According to one embodiment of the method according to the invention, the fermentation is subsequently carried out without further addition of production medium.

According to one advantageous embodiment of the method according to the invention, production medium, and more particularly the carbon source, is added sequentially during the culture step to maintain and optimize productivity.

The aqueous production medium used in the culture step according to the invention is preferentially prepared in ultrapure water having a conductivity between 15 and 18 MegaOhms, advantageously 18 MegaOhms.

The production medium used in the culture step according to the invention is also sterilized so as to reduce the risk of contaminations.

The carbon source is preferentially chosen from glucose, mannose, sucrose, xylose, maltose, fructose and glycerol, taken alone or in combination, preferentially glucose.

The carbon source is preferentially used at a concentration of 30 to 150 g/L, for example 45, 60, 75, 90 or 120 g/L, more preferentially 60 g/L for glucose.

The nitrogen source is preferentially chosen from ammonium nitrate $NH_4NO_3$, sodium nitrate $NaNO_3$, ammonium sulfate $(NH_4)_2SO_4$, peptones (for example Bacton™ peptone (Difco)) or a natural amino acid, taken alone or in combination, preferentially ammonium nitrate $NH_4NO_3$.

The nitrogen source is preferentially used at a concentration of 0.1% to 1% (weight/volume), for example 0.1%, 0.2% or 0.5%, more preferentially 0.1% $NH_4NO_3$.

The mineral salts in solution are preferentially chosen from magnesium, phosphate, potassium, sodium, chloride, sulfate ions, taken alone or in combination.

By way of illustrative example, the mineral salt solution is a mixture of $KH_2PO_4$, KCl, $MgSO_4$ and HCl.

The sterilized aqueous production medium defined and used in the culture step according to the invention also contains a calcium source, preferentially at a concentration in the production medium between 2 and 100 mM, more preferentially 50 mM.

The calcium source is preferentially chosen from at least 98% pure precipitated calcium carbonate $CaCO_3$ comprising at least one trace element, solubilized under acidic conditions and added to the mineral salt solution extemporaneously, or calcium chloride $CaCl_2$ in the presence of a trace element solution. Insofar as the $CaCO_3$ is used pure, for example at 100%, and comprises no trace elements, it is used in combination with at least one trace element.

The trace element associated with the calcium source is preferentially chosen from manganese, copper, cobalt, iron, zinc, strontium, lead, mercury, chlorine, boron, molybdenum and sulfur, for example iron and/or manganese, taken alone or in combination.

The concentration of trace element(s), taken alone or in combination, in the production medium is preferentially not more than in the region of 0.1 mM.

One major and essential difference with the prior art, besides the specific choice of the strain of interest *Aureobasidium pullulans* CBS 771.97 or related strains thereof, is the use in the production medium of a calcium source advantageously in the form of $CaCO_3$ or $CaCl_2$ in the presence of at least one trace element, preferentially manganese. Indeed, unlike the cited prior art wherein the presence of $CaCO_3$ increases the production of polymalic acid but reduces the quantity of lipids of interest produced, in the method according to the invention, the Applicant demonstrated the essential and unexpected role of this compound in the production of metabolites and more particularly of sucrolipids, and consequently lactones, and more particularly of (R)-5,6-dihydro-6-pentyl-2H-pyran-2-one (or (R)-(−)-*massoia* lactone) and/or a hydroxylactone, i.e. (4R,6R)-4-hydroxy-6-pentyl-tetrahydro-2H-pyran-2-one.

The effect of calcium is thus unexpected in the method according to the invention, and the opposite of that known of $CaCO_3$ in the prior art.

According to one advantageous example of an embodiment according to the invention, a study of the optimal concentrations for precipitated $CaCO_3$ (Rectapur™ Prolabo No. 22296.294) having a purity greater than or equal to 98% made it possible to determine that, at low concentrations (0.02%), it already enables an enhancement of the yield and that, at higher concentrations (0.5%), it is further most likely responsible for the settling of the oily phase of interest comprising the lactone precursors subsequently converted into (R)-5,6-dihydro-6-pentyl-2H-pyran-2-one et/or (4R,6R)-4-hydroxy-6-pentyl-tetrahydro-2H-pyran-2-one. The presence of these precursors was demonstrated. It is possible that the lactone is also formed spontaneously in small quantities, particularly in the case of long-term storage.

Advantageously, the production medium further contains a vitamin source.

The vitamin source is preferentially chosen from a yeast extract, for example Bacto™ Yeast extract (Difco) or a vitamin B complex.

By way of non-limiting example of a particularly preferred production medium according to the invention wherein a volume of the pre-culture of *Aureobasidium pullulans* CBS 771.97 or related strains thereof is inoculated:

the carbon source is 60 g/L glucose prepared in ultrapure water and sterilized at 115° C.;

the nitrogen source and the mineral salt solutions are prepared in ultrapure water and sterilized at 120° C. and contain a mixture of 1 g/L of $NH_4NO_3$, 0.1 g/L of $KH_2PO_4$, 0.5 g/L of KCl, 0.2 g/L of $MgSO_4$, $7H_2O$, and further 0.5 g/L of yeast extract as a vitamin source (Bacto™ Yeast extract (Difco)); and 0.5% (weight/volume) $CaCO_3$ (Rectapur™ Prolabo No. 22296.294) is solubilized in ultrapure water acidified with hydrochloric acid, at a pH of approximately 5, and then is added to the mineral salt solution after sterilization by autoclaving.

According to a further example, if the calcium source is $CaCl_2$ in solution with trace elements, it is prepared in ultrapure water and sterilized by filtering via a sterile 0.2 μm filter.

This culture step in liquid medium thus enables the production of biomass (cells) and metabolites.

The metabolites produced during the culture step are essentially sucrolipids. The Applicant particularly identified the production of sucrolipids based on dihydroxydecanoic acid monomer, and more particularly the production of 21 metabolites, notably halymecin, halymecin-arabitol, halymecin-mannitol and exophilin-mannitol.

In the method according to the invention, following the fermentation period, the metabolites produced are converted into a lactone mixture comprising (R)-5,6-dihydro-6-pentyl-2H-pyran-2-one and/or (4R,6R)-4-hydroxy-6-pentyl-tetrahydro-2H-pyran-2-one. More particularly, the metabolites produced are converted into a lactone mixture by hydrolyzing into an acidic or basic medium, or by enzymatic hydrolysis, the sucrolipids produced into monomers, and by cyclizing same to obtain a lactone mixture comprising (R)-5,6-dihydro-6-pentyl-2H-pyran-2-one and/or (4R,6R)-4-hydroxy-6-pentyl-tetrahydro-2H-pyran-2-one which are suitable for assay by means of gas chromatography.

It is advisable to treat the entire culture medium to obtain the target lactones so as to avoid problems in terms of reproducibility of the results due to the heterogeneity of the medium which increases with the quantity of sucrolipids produced insofar as only one aliquot is extracted.

Alternatively, the entire culture medium may advantageously be centrifuged so as to remove the supernatant and treat the pellet retrieved containing the cells and sucrolipids produced to obtain the target lactones. Indeed, the conversion is thus separated from the sucrolipid production and these steps may thus be advantageously performed on two different sites. Furthermore, the volumes to be treated are smaller and thus require less cumbersome equipment.

According to a first mode for converting the metabolites produced, following the fermentation period, on the entire culture medium or advantageously on the pellet after centrifugation, saponification of the sucrolipids is performed, for example by adding 4N sodium hydroxide NaOH, followed by acidification, for example by adding 50% sulfuric acid $H_2SO_4$ and heating, for example to 90° C. for 4 hours. A mixture of (R)-5,6-dihydro-6-pentyl-2H-pyran-2-one (or (R)-(−)-*massoia* lactone) and a hydroxylactone, i.e. (4R, 6R)-4-hydroxy-6-pentyl-tetrahydro-2H-pyran-2-one, is obtained wherein the proportions vary according to the acid concentration, the temperature and the heating time. The ratio of (R)-(−)-*massoia* lactone/hydroxylactone increases when the acid concentration, the heating temperature and/or time are increased. In addition, hydroxylactone generally remains present following the treatment and may be advantageously dehydrated to (R)-5,6-dihydro-6-pentyl-2H-pyran-2-one of interest.

According to a second advantageous mode for converting the metabolites produced, following the fermentation period, the culture medium is directly acidified, for example by adding 50% sulfuric acid $H_2SO_4$ (final normality 1.2 N), citric acid or tartaric acid, and heated, for example between 90° C. and 110° C. for 12 hrs to 24 hrs. The hydrolysis of the sucrolipids (monomer formation) is concurrently followed by the lactonization and dehydration of the monomers formed to obtain the (R)-5,6-dihydro-6-pentyl-2H-pyran-2-one (or (R)-(−)-*massoia* lactone) of interest. The three reactions are performed simultaneously. Hydroxylactone may be present if the reaction conditions (temperature, acid normality, time) are not sufficient. The ratio of (R)-(−)-*massoia* lactone/hydroxylactone increases when the acid concentration, the heating temperature and/or time are increased. If hydroxylactone remains present following the treatment, it may be advantageously dehydrated to the (R)-(−)-*massoia* lactone of interest. Even more advantageously, this conversion mode is applied to the pellet.

According to a third mode for converting the metabolites produced, following the fermentation period, the culture medium or the pellet obtained after centrifugation is extracted with a solvent. By way of example, ethyl acetate is used as long as the medium is not acidified, the sucrolipids being stable in ethyl acetate but not lactones. The solvent is then evaporated and, using the sucrolipids extracted, saponification, acidification and heating are performed according to the first embodiment or acidification and heating are performed directly according to the second embodiment. It is also possible to carry out thermal conversion at approximately 250° C.

Further conversion modes may also be envisaged. For example, the pellet containing metabolites produced may be extracted with supercritical $CO_2$ and the (R)-5,6-dihydro-6-pentyl-2H-pyran-2-one (or (R)-(−)-*massoia* lactone) of interest obtained directly.

As such, insofar as, according to the chosen conversion conditions, a mixture of (R)-5,6-dihydro-6-pentyl-2H-pyran-2-one and (4R,6R)-4-hydroxy-6-pentyl-tetrahydro-2H-pyran-2-one is obtained, the method according to the invention further comprises a step whereby the hydroxylactone obtained is converted to the (R)-5,6-dihydro-6-pentyl-2H-pyran-2-one of interest by dehydrating same, for example in the presence of an acid after solubilizing in an organic solvent.

Finally, the obtained (R)-5,6-dihydro-6-pentyl-2H-pyran-2-one of interest is isolated by extraction with an organic solvent such as for example methyl t-butyl ether, methyl ethyl ketone, ethyl acetate, chloroform, dichloromethane and dimethyl carbonate followed by distillation, or by extraction with supercritical $CO_2$, or by hydrodistillation.

The (R)-5,6-dihydro-6-pentyl-2H-pyran-2-one (or (R)-(−)-*massoia* lactone) of interest, suitable for use as such, is thus retrieved.

The method according to the invention is thus suitable for obtaining (R)-(−)-*massoia* lactone having a characteristic coconut milk and flesh fragrance true to that of the (R)-(−)-*massoia* lactone obtained from *Cryptocaria massoia* tree bark oil. The (R)-(−)-*massoia* lactone produced using the method according to the invention is thus suitable for use as such as a flavor or fragrance in food products, beverages, or others. Furthermore, it is produced by means of a biotechnological process according to the method according to the invention at a low cost, in large quantities suitable for meeting market demand and according to a method complying with environmental constraints.

The advantages of the method for producing lactones, and particularly (R)-5,6-dihydro-6-pentyl-2H-pyran-2-one (or (R)-(−)-*massoia* lactone), according to the invention are demonstrated by the results of the examples hereinafter and illustrated by FIGS. 2 to 7.

EXAMPLE 1

By way of illustrative example of the production method according to the invention, the Applicant screened, in a comparative study, various strains of *Aureobasidium* of different clades, according to the operating conditions of production developed according to the invention for obtaining satisfactory reproducibility so as to determine the productivity in respect of lactones by the various available strains tested.

The Applicant thus purchased a plurality of strains of *Aureobasidium*, as listed in table 1 hereinafter.

TABLE 1

| Summary of all strains tested | |
|---|---|
| Strain ID | Name |
| CBS 771.97 | *Aureobasidium pullulans* var. *pullulans* |
| CBS 585.75 | *Aureobasidium pullulans* var. *pullulans* |
| CBS 584.75 | *Aureobasidium pullulans* var. *pullulans* |
| CBS 123.33 | *Exophiala lacanii-corni* (*A. pullulans* until 1967) |
| CBS 117.466 | *Aureobasidium pullulans* |
| CBS 147.97 | *Aureobasidium pullulans* var. *namibiae* |

The operating conditions of the example of the method according to the invention embodied in this study are more particularly described hereinafter and are identical for all the strains screened.

A pre-culture is produced from a cryotube of each of the screened strains according to the following steps:
- step 1: a malt extract peptone agar tube (solid ME medium: MEA Fluka™) is inoculated, incubated at 25° C. with growth until colonies appear;
- step 2: using this tube, a Petri dish containing a solid ME medium (MEA Fluka™) is inoculated in streaks, and the dish is inoculated at 25° C. for 24 hrs; and
- step 3: after growth on the dish, a clone is inoculated in a 5 mL liquid malt extract tube (liquid ME medium), incubated at 25° C. under stirring at 200 rpm for 18 hours.

On the following day, all the tubes containing the same strain are combined and an Optical Density (OD) reading performed.

The pre-culture produced in this way is then used for inoculating flasks for the following fermentation culture step. In this study, the size of the inoculum is fixed so as to obtain an initial OD value of the culture of 0.5.

On the basis of the growth of each of the strains screened, the volume of pre-culture inoculated per flask varies slightly as illustrated in table 2 hereinafter:

TABLE 2

Volume of pre-culture required for each strain tested

| Strain | OD 600 nm | V inoculation for $OD_{initial} = 0.5$ |
| --- | --- | --- |
| CBS 771.97 | 5 | 3 mL |
| CBS 585.75 | 7.6 | 2 mL |
| CBS 584.75 | 7.6 | 2 mL |
| CBS 123.33 | 8.7 | 1.7 mL |
| CBS 117.466 | 9.5 | 1.7 mL |
| CBS 147.97 | 5 | 3 mL |

As such, using the pre-culture produced for each strain, the volume of pre-culture determined for each strain (see table 2) is inoculated into 300 mL baffled flasks containing 30 mL of production medium comprising:
- a carbon source consisting of 60 g/L glucose prepared in ultrapure water and sterilized separately at 115° C.;
- a nitrogen source and a mineral salt source prepared in ultrapure water and sterilized at 120° C. comprising:
  $NH_4NO_3$: 1 g/L;
  $KH_2PO_4$: 0.1 g/L;
  KCl: 0.5 g/L;
  $MgSO_4$, $7H_2O$: 0.2 g/L; and
- a 0.5 g/L yeast extract (Bacto™ Yeast extract (Difco)) as a vitamin source; and
- 5 g/L of precipitated calcium carbonate $CaCO_3$ (Rectapur™ Prolabo No. 22296.294) solubilized in ultrapure water acidified with hydrochloric acid, at a pH in the region of 5, and added to the salt solution extemporaneously.

The culture step of the various screened strains is then carried out at two fermentation temperatures, 25° C. and 30° C.

The flasks are thus incubated in parallel at 25 and 30° C., under stirring (140 rpm).

The flasks are stopped at 3, 5 and 7 days of culture in order to determine the yield of total lactones produced, i.e. a mixture of (R)-5,6-dihydro-6-pentyl-2H-pyran-2-one and/or (4R,6R)-4-hydroxy-6-pentyl-tetrahydro-2H-pyran-2-one, for each strain tested.

The fermentation medium of each flask is then saponified overnight by adding 4N NaOH, then acidified with 50% $H_2SO_4$ and finally heated to 90° C. for 1 hour.

The mixture of lactones produced is retrieved by extraction with methyl t-butyl ether.

The organic phase is injected in gas chromatography for a quantitative analysis of the lactones produced.

All the results obtained for screening the different strains of *Aureobasidium* within the scope of this study are reported in table 3 hereinafter.

TABLE 3

Monitoring of the total lactone yield of the different strains screened according to the method according to the invention at 25° C. and 30° C.

| | 25° C. (g/L) | | | 30° C. (g/L) | | |
| --- | --- | --- | --- | --- | --- | --- |
| Strain ID | D3 | D5 | D7 | D3 | D5 | D7 |
| CBS 771.97 | 5.2 | 9.5 | 10.6 | 6.1 | 10.3 | 13.0 |
| CBS 585.75 | ND | 1.2 | 0.8 | 0 | 0.04 | 0.2 |
| CBS 584.75 | 1.5 | 2.4 | 5.2 | 0.58 | 0.6 | 0.8 |
| CBS 123.33 | 0.45 | 0.6 | 0.9 | 0.51 | 0.6 | 0.7 |
| CBS 117.466 | 0 | 0 | 0 | 0 | 0 | 0 |
| CBS 147.97 | 1.2 | 2.2 | 2.8 | 0 | 0 | 0 |

ND: Not determined

Figure 2:
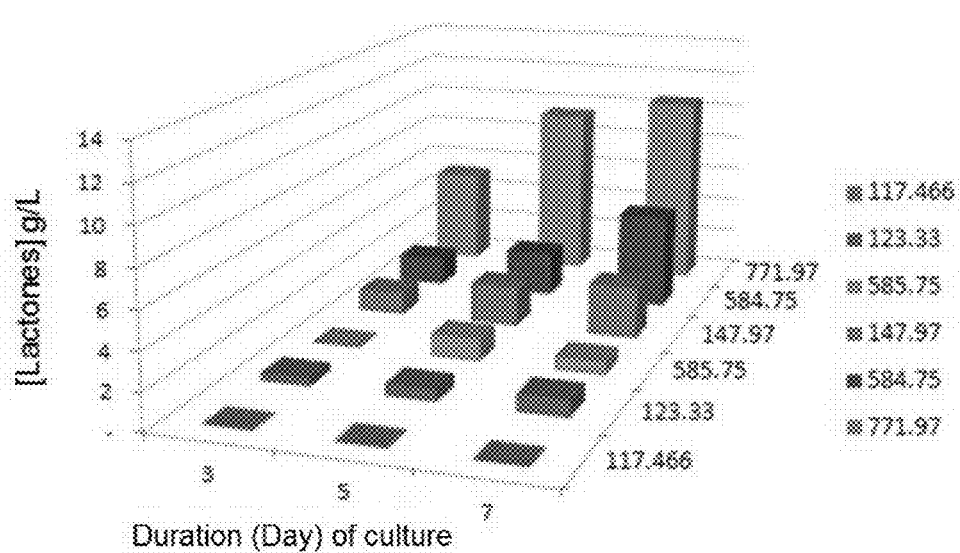
FIG. 2 is a histogram representing the monitoring of lactone production according to an example of the method according to the invention with different *Aureobasidium* strains in culture at 25° C.
Figure 3:
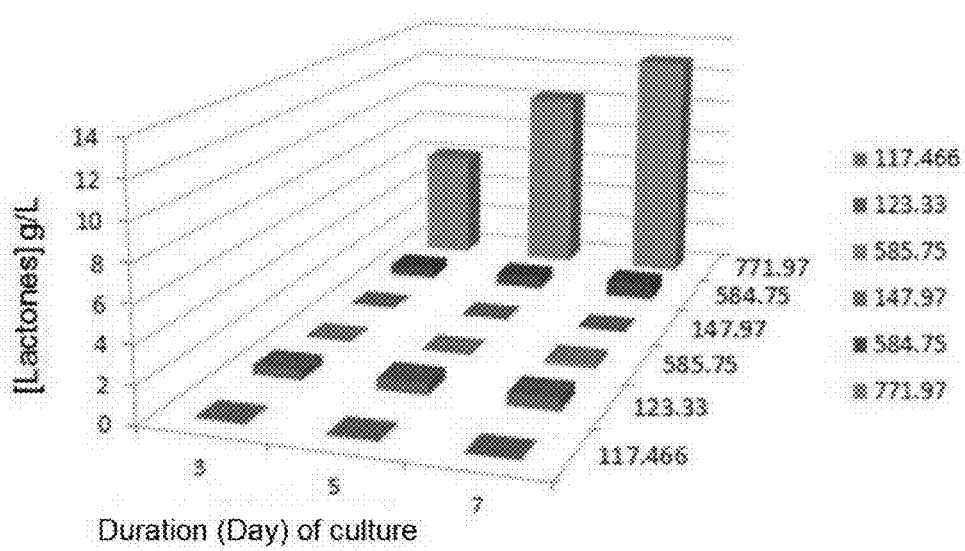
FIG. 3 is a histogram representing the monitoring of lactone production according to the same example of the method according to the invention with different *Aureobasidium* strains in culture at 30° C.

The results of the comparative study listed in table 3 above are more particularly illustrated by FIGS. 2 and 3.

FIG. 2 represents in histogram form the monitoring of the yield of lactones produced, i.e. a mixture of (R)-5,6-dihydro-6-pentyl-2H-pyran-2-one and/or (4R,6R)-4-hydroxy-6-pentyl-tetrahydro-2H-pyran-2-one, after 3, 5 and 7 days of culture, by each of the *Aureobasidium* strains tested by fermentation at 25° C.

Similarly, FIG. 3 represents in histogram form the monitoring of the yield of lactones produced, i.e. a mixture of (R)-5,6-dihydro-6-pentyl-2H-pyran-2-one and/or (4R,6R)-4-hydroxy-6-pentyl-tetrahydro-2H-pyran-2-one, after 3, 5 and 7 days of culture, by each of the *Aureobasidium* strains tested by fermentation at 30° C.

As such, the lactone production by each of the strains tested using the method according to the invention is evaluated.

The effect of increasing the fermentation temperature during the culture step of the method according to the invention was thus tested for all the strains in terms of yield of lactones produced.

To this end, of all the strains tested, it is noted, as illustrated by FIGS. 2 and 3 in particular, that the strain CBS 771.97 proves to have the highest lactone production from D3, whether at 25° C. or at 30° C., and on D5 and likewise until D7.

With fermentation at 25° C., the yield of lactones produced is at least 3 times greater for the strain CBS 771.97 in relation to the other strains on D3 and D5, and at least 2 times greater on D7.

Similarly, the difference in yield is even more pronounced with fermentation at 30° C., the yield of lactones produced is at least 10 times greater for the strain CBS 771.97 in relation to the other strains on D3, at least 5 times greater on D5, and at least 7 times greater on D7.

It is also observed that some strains are insensitive to temperature in terms of production. This is the case for example of the strain CBS 117.466 which does not produce sucrolipids and thus lactone at either of the two fermentation temperatures tested or the strain CBS 123.33, which produces a minimal quantity of lactones and similar to 25° C. and 30° C.

Furthermore, increasing the fermentation temperature for some strains appears to have a negative effect on the lactone yield. This is observed clearly for the strain CBS 147.97 where increasing the fermentation temperature from 25° C. to 30° C. has a drastic effect in terms of production. Indeed, the strain no longer produces lactone at 30° C., compared to 25° C. where the yield is up to 2.8 g/L on D7. Further strains, such as for example the strain CBS 584.75 are also sensitive to increasing the temperature: it produces 6 times less lactones at 30° C. compared to 25° C. on D7. Moreover, this negative effect is noteworthy from D3. The strain CBS 585.75 also belongs to the group of strains for which increasing the temperature has a negative effect on the total lactone yield.

However, surprisingly and advantageously, it appears that a positive effect of increasing the temperature is only observed for the strain CBS 771.97, which produces even more lactones with fermentation at 30° C. compared to 25° C. with a significant increase of 22.6% on D7, unlike all the strains screened.

A specificity of the strain CBS 771.97 or the related strains thereof (clade No. 7) is thus observed according to the method according to the invention.

EXAMPLE 2

An additional study on the effect of increasing the fermentation temperature in the method according to the invention on the lactone yield was more particularly conducted for the strain more particularly of interest, i.e. *Aureobasidium pullulans* CBS 771.97, on the basis of the same operating conditions as those of the comparative study above.

Figure 4:
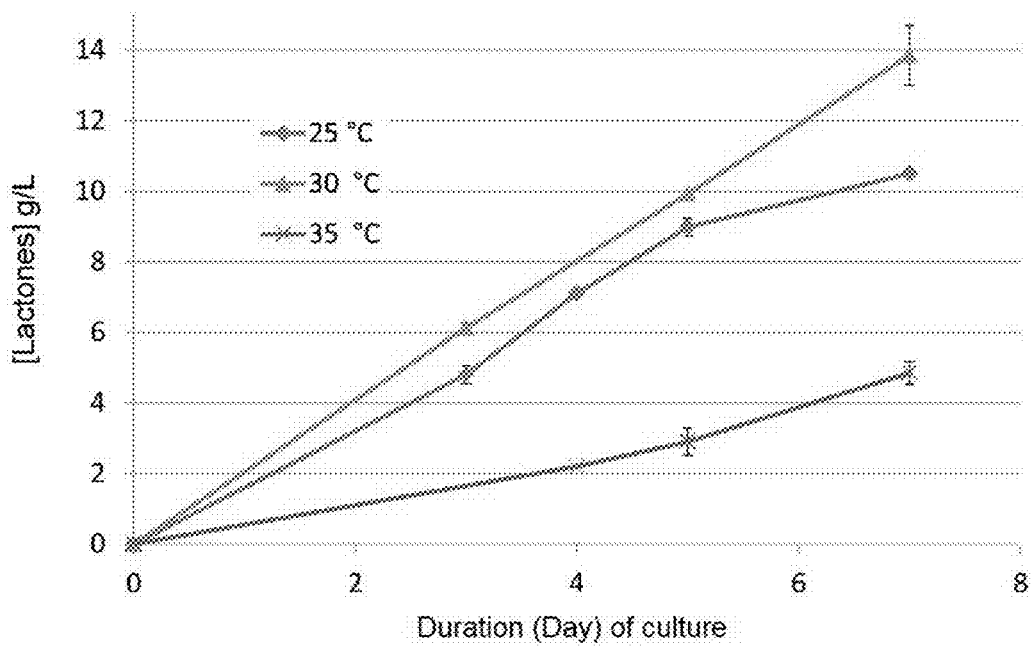
FIG. 4 is a graph representing the effect of the temperature of the culture step on lactone production according to an example of the method according to the invention for the *Aureobasidium pullulans* strain CBS 771.97.

The yields of lactones produced obtained in this additional study are listed in table 4 hereinafter and illustrated by FIG. 4 representing the effect of the temperature of the culture step on lactone production according to an example of the method according to the invention for the *Aureobasidium pullulans* strain CBS 771.97.

TABLE 4

Study of increasing the temperature of lactone production

| T (° C.) | Total lactones (g/L) | | | |
|---|---|---|---|---|
| | D3 | D4 | D5 | D7 |
| 25 | 4.8 | 7.1 | 9 | 10.5 |
| 30 | 6.1 | | 9.9 | 13.9 |
| 35 | | 2.2 | 2.9 | 4.9 |

On the basis of the results obtained, a positive effect of increasing the fermentation temperature to 30° C. is observed, compared to 25° C. and 35° C., on the yield of lactones produced using the *Aureobasidium pullulans* strain CBS 771.97 from D3, and more particularly on D7 with significant increases of 32.4% and 183.7%, respectively.

Furthermore, the yields obtained in this additional study demonstrate the satisfactory reproducibility of the method according to the invention in that the yields of lactones produced obtained at 25° C. and 30° C. under similar culture conditions vary by merely 8.3% (D3) and 1% (D7) at 25° C., and are identical (D3) and vary by merely 6.9% (D7) at 30° C. between the results obtained in this additional study and those obtained in the comparative study in example 1 for this strain CBS 771.97.

The operating conditions used by the Applicant and the presence in particular of calcium in the aqueous production medium thus promote the production of sucrolipids and hence of lactones, in particular (R)-(−)-*massoia* lactone, by the *Aureobasidium pullulans* strain CBS 771.97. The operating conditions embodied in the method according to the invention which consist of operations commonly carried out by those skilled in the art, are thus very easy to implement.

The method according to the invention further has a satisfactory reproducibility and enhanced lactone productivity (enhanced quantity of lactone formed and production rate), in particular (R)-(−)-*massoia* lactone. To this end, it is noted that with this strain CBS 771.97 or the related strains thereof, the metabolites produced are advantageously not rapidly degraded after having reached a peak and may be converted to (R)-5,6-dihydro-6-pentyl-2H-pyran-2-one (or (R)-(−)-*massoia* lactone) and/or (4R,6R)-4-hydroxy-6-pentyl-tetrahydro-2H-pyran-2-one.

Figure 5:
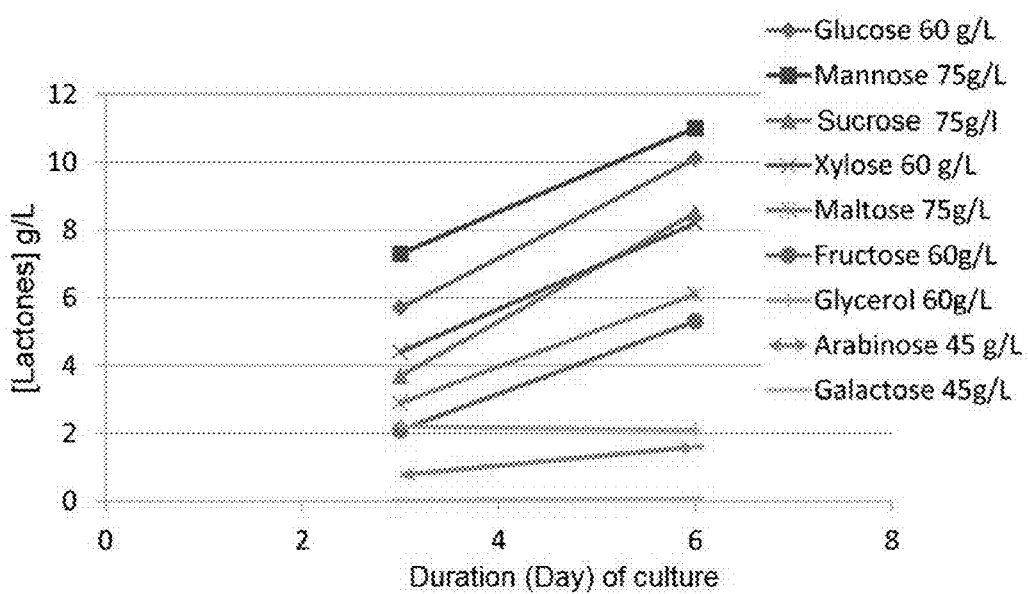
FIG. 5 is a graph representing the effect of the carbon source on lactone production according to an example of the method according to the invention for the *Aureobasidium pullulans* strain CBS 771.97.

The Applicant also demonstrated the effect of the carbon source (example 3), as illustrated in FIG. 5, on lactone production according to an example of the method according to the invention using the *Aureobasidium pullulans* strain CBS 771.97.

EXAMPLE 3

The effect of the carbon source on lactone production was tested on the basis of the operating conditions of example 1 using the *Aureobasidium pullulans* strain CBS 771.97 by means of culture at 25° C. This is more particularly illustrated in FIG. 5.

In FIG. 5, it is observed that, of the carbon sources tested, arabinose and galactose (at 45 g/L) are not suitable for significant lactone production according to the method according to the invention. It is important to note that the yields obtained are also similar or lower at arabinose or galactose concentrations of 60 or 75 g/L.

On the other hand, the carbon source of the production medium of the method according to the invention chosen from glycerol, fructose, maltose, xylose, sucrose, glucose and mannose, at a concentration of 60 or 75 g/L, produces significant yields of lactones produced of at least 2 g/L for glycerol after 6 days of culture by fermentation at 25° C. and likewise up to 11 g/L for mannose on D6.

On the basis of the results obtained, the carbon source preferentially used is 60 g/L glucose which has the best ratio of metabolites produced (lactones produced)/cost.

EXAMPLE 4

The Applicant also monitored the lactone production, productivity and glucose consumption on the basis of the operating conditions of example 1 using the *Aureobasidium pullulans* strain CBS 771.97 by means of culture at 25° C. over a period of 20 days of culture, as illustrated in FIG. 6.

The lactone production peak, in the region of 9 g/L, was reached after 7 days of culture. Accounting for measurement errors, a plateau can be considered to exist between 7 and 10 days.

In terms of productivity, the peak is reached at 5 days and then drops.

The disappearance of glucose in the culture medium appears to be concurrent to the drop in productivity.

EXAMPLE 5

For this purpose, according to one advantageous embodiment of the method according to the invention, sequential addition of the production medium, and more particularly of the carbon source, and notably of glucose, during the culture step was tested using the *Aureobasidium pullulans* strain CBS 771.97 on the basis of the operating conditions of example 1 by introducing a fourth pre-culture step. The pre-culture produced in step 3 is used for inoculating three flasks in turn used as a pre-culture for two 1 L fermenters. The culture step is then carried out at 28° C. in a fermenter, with aeration of 0.5 vvm and stirring of 500 rpm, over a period of 15 days of culture.

In the first fermenter, the carbon source, more particularly glucose, is obtained from the production medium (60 g/L). In the second fermenter, in addition to the 60 g initially contained in the production medium, 30 g of glucose in the form of a sterile 500 g/L aqueous solution was respectively added during the culture step on D3 and D7.

The monitoring of lactone production and glucose consumption are more particularly illustrated in FIG. 7.

An increase in the quantity of lactones produced over time is thus observed when glucose is added sequentially, that is both greater and more rapid than in the absence of adding glucose during the culture step. As such, on D7, a 38% increase in the quantity of lactones produced is observed, the increase being 57% on D12.

Sequential addition of the production medium, and more particularly of the carbon source, and notably for example of glucose, during the culture step is thus suitable for maintaining a high productivity over a longer period, i.e., in this example, of more than 5 days.

Obviously, the invention is not restricted to the embodiments and the examples presented above and those skilled in the art, by means of routine operations, may be led to create further embodiments not described explicitly, which fall within the broad scope of the invention.

The invention claimed is:

1. A method for producing lactones from a strain of *Aureobasidium pullulans*, comprising:
    producing a pre-culture of an *Aureobasidium pullulans* strain selected from the group consisting of *Aureobasidium pullulans* CBS 771.97 obtained from CBS-KNAW Fungal Biodiversity Centre, Uppsalalaan 8, 3584 CT Utrecht, Netherlands, and strains of *Aureobasidium pullulans* from the clade of CB S771.97, to obtain an inoculum;
    from the inoculum obtained from the pre-culture, producing a culture by fermentation at a temperature in a range of from 20° C. to 40° C. over a period of at least 3 days to produce metabolites, in a sterilized aqueous production medium containing:
        a carbon source;
        a nitrogen source;
        a mineral salt solution; and
        a calcium source, at a concentration in a range of from 2 to 100 mM; and
    following the fermentation, converting the metabolites produced into a lactone mixture comprising (R)-5,6-dihydro-6-pentyl-2H-pyran-2-one and/or (4R,6R)-4-hydroxy-6-pentyl-tetrahydro-2H-pyran-2-one.

2. The method according to claim 1, comprising converting the (4R,6R)-4-hydroxy-6-pentyl-tetrahydro-2H-pyran-2-one obtained to (R)-5,6-dihydro-6-pentyl-2H-pyran-2-one by dehydration.

3. The method according to claim 1, further comprising isolating the (R)-5,6-dihydro-6-pentyl-2H-pyran-2-one obtained by extraction with an organic solvent followed by distillation, or by extraction with supercritical $CO_2$, or by hydrodistillation.

4. The method according to claim 1, wherein the pre-culture producing is carried out using a cryotube of the *Aureobasidium pullulans* strain in a solid and/or liquid medium selected from the group consisting of (i) a malt extract medium and (ii) a YNB ("Yeast Nitrogen Base") medium.

5. The method according to claim 1, wherein a volume of pre-culture of the *Aureobasidium pullulans* strain is inoculated in the production medium in relation to an initial Optical Density (OD) of the culture medium in a range of from 0.5 to 2.

6. The method according to claim 5, wherein a volume of the inoculum is in a range of from 3 to 10% of a volume of the culture medium.

7. The method according to claim 1, wherein the producing by fermentation culture is carried out at a temperature in a range of from 25° C. to 35° C.

8. The method according to claim 1, wherein the producing by fermentation culture is carried out under stirring for a period in a range of from 3 to 20 days.

9. The method according to claim 1, wherein a calcium concentration in the production medium is 50 mM.

10. The method according to claim 1, wherein the calcium source is chosen from (i) at least 98% pure precipitated calcium carbonate $CaCO_3$ comprising at least one trace element, solubilized under acidic conditions and added to a mineral salt solution extemporaneously, and (ii) calcium chloride $CaCl_2$ in the presence of a trace element solution.

11. The method according to claim 10, wherein the trace element is chosen from the group consisting of manganese, copper, cobalt, iron, zinc, strontium, lead, mercury, chlorine, boron, molybdenum, sulfur, and combinations thereof.

12. The method according to claim 1, wherein:
    the carbon source is chosen from the group consisting of glucose, mannose, sucrose, xylose, maltose, fructose, glycerol, and combinations thereof;
    the nitrogen source is chosen from the group consisting of ammonium nitrate $NH_4NO_3$, sodium nitrate $NaNO_3$, ammonium sulfate $(NH_4)_2SO_4$, peptones, natural amino acids, and combinations thereof; and
    the mineral salts in solution are chosen from the group consisting of magnesium, phosphate, potassium, sodium, chloride, sulfate ions, and combinations thereof.

13. The method according to claim 1, wherein the production medium further contains a vitamin source.

14. The method according to claim 5, wherein a volume of pre-culture of the *Aureobasidium pullulans* strain is inoculated in the production medium in relation to an initial Optical Density (OD) of 0.5.

15. The method according to claim 7, wherein the producing by fermentation culture is carried out at a temperature in a range of from 28° C. to 30° C.

16. The method according to claim 8, wherein the producing by fermentation culture is carried out under stirring for a period in a range of from 7 to 15 days.

17. The method according to claim 12, wherein:
    the carbon source is glucose; and
    the nitrogen source is ammonium nitrate $NH_4NO_3$.

18. The method according to claim 2, further comprising isolating the (R)-5,6-dihydro-6-pentyl-2H-pyran-2-one obtained by extraction with an organic solvent followed by distillation, or by extraction with supercritical $CO_2$, or by hydrodistillation.

19. The method according to claim 2, wherein the pre-culture producing is carried out using a cryotube of the *Aureobasidium pullulans* strain in a solid and/or liquid medium chosen from (i) a malt extract medium and (ii) a YNB ("Yeast Nitrogen Base") medium.

20. The method according to claim 3, wherein the pre-culture producing is carried out using a cryotube of the *Aureobasidium pullulans* strain in a solid and/or liquid medium chosen from (i) a malt extract medium and (ii) a YNB ("Yeast Nitrogen Base") medium.

21. The method according to claim 1, wherein the *Aureobasidium pullulans* strain is selected from the group consisting of RSU28, CU3, DOUG, NRRLY-6220, RSU25, BM1, and RSU16.

22. The method according to claim 1, wherein the *Aureobasidium pullulans* strain is *Aureobasidium pullulans* CBS 771.97 obtained from CBS-KNAW Fungal Biodiversity Centre, Uppsalalaan 8, 3584 CT Utrecht, Netherlands.

* * * * *